United States Patent [19]

Hurst

[11] 4,026,764

[45] May 31, 1977

[54] DRY ISOMERASE ACTIVATION

[75] Inventor: Thomas L. Hurst, Decatur, Ill.

[73] Assignee: A. E. Staley Manufacturing Company, Decatur, Ill.

[22] Filed: Mar. 20, 1975

[21] Appl. No.: 560,658

[52] U.S. Cl. .............................. 195/31 F; 195/62; 195/63; 195/65; 195/66 R; 195/68; 195/114

[51] Int. Cl.$^2$ ........................................ C12D 13/00

[58] Field of Search .................. 195/31 F, 62, 66 R, 195/63, 68, 114

[56] References Cited

UNITED STATES PATENTS

| | | | |
|---|---|---|---|
| 3,623,953 | 11/1971 | Cotter et al. | 195/31 F |
| 3,694,314 | 9/1972 | Lloyd et al. | 195/31 F |
| 3,821,082 | 6/1974 | Lamm et al. | 195/31 F |

OTHER PUBLICATIONS

Danno et al. "Studies on D–Glucose–Isomerizing Activity of D–Xylose–Grown Cells from Bacillus Coagulans, Strain HN–68 Part II, Purification and Properties of D–Glucose–Isomerizing Enzyme," *Agr. Biol. Chem.*, vol. 31, No. 3 pp. 284–292 (1967).
Tsumura et al., "Enzymatic Conversion of D–Glucose to D–Fructose Part IX. Dehydration and Preservation of the Cell as Enzyme Source," *Agr. Biol. Chem.*, vol. 31, No. 8, pp. 908–910 (1967).
Danno et al., "Studies on D–Glucose–Isomerizing Enzyme from Bacillus Coagulans, Strain HN–68 Part VI, The Role of Metal Ions on the Isomerization of D–Glucose and D–Xylose by the Enzyme", *Agr. Biol. Chem.*, vol. 35, No. 7, pp. 997–1006 (1971).
Tsumura et al., "Enzymatic Conversion of D–Glucose to D–Fructose Part VIII, Propagation of Streptomyces Phaechromogenus in the Presence of Cobaltous Ion", *Agr. Biol. Chem.*, vol. 31, No. 8, pp. 902–907 (1967).

*Primary Examiner*—Alvin E. Tanenholtz
*Assistant Examiner*—T. G. Wiseman
*Attorney, Agent, or Firm*—M. Paul Hendrickson; Charles J. Meyerson

[57] ABSTRACT

The isomerase activity of a dry isomerase preparation (e.g., glucose isomerase) is enhanced by initially pretreating the isomerase in an aqueous solution which contains an activating amount of a metal ion activator and/or a thiol generating reducing agent and/or a monosaccharide which the isomerase is capable of isomerizing. Pretreatment temperature and time periods are most suitably conducted in such a manner so as to minimize isomerase deactivation. The pretreatment increases total isomerase activity and thereby renders it more effective for use in an isomerization process (e.g., glucose isomerization).

18 Claims, No Drawings

DRY ISOMERASE ACTIVATION

BACKGROUND OF THE INVENTION

It is well-known that certain enzymes convert aqueous aldose monosaccharides to ketose monosaccharides and vice versa. Within recent years, isomerases have attracted considerable commercial interest in glucose syrup isomerization reactions. Such enzymes are frequently referred to by the trade as glucose isomerases. Most isomerases can isomerize a plurality of aldose and/or ketose monosaccharide substrates. For example, many glucose isomerases can also isomerize xylose.

Fully hydrated glucose isomerases will deactivation upon storage. Deactivation is accelerated at elevated temperatures. An isomerase manufacturer will, therefore, customarily retail it as a dry isomerase. In order to use this dry isomerase in an isomerization process, the isomerized syrup manufacturer must convert it to the hydrated form.

A typical commercial glucose isomerization process results in an isomerized glucose syrup product containing approximately 45–55 parts fructose and 55–45 parts glucose. The glucose isomerization process normally requires from about 24 to 72 hours and will be conducted at temperatures above 50° C. (usually between 60° to 70° C.). Achieving and maintaining sufficient isomerase activity throughout the isomerization process is necessary in order to obtain the desired high fructose yield.

Unfortunately, isomerases are inherently susceptible to deactivation especially when employed for prolonged periods at the elevated isomerization media temperature as required to achieve optimum dextrose isomerization. In batch processes, reduced isomerase activity is normally compensated by charging the reactor with a sufficiently large enough isomerase dosage to permit the isomerization reaction to proceed to completion. In a continuous isomerization process, isomerase deactivation may be partially corrected by periodic addition of fresh isomerase to the isomerization reactor. This isomerase deactivation problem creates difficulties and additional expense in the manufacture of isomerized glucose syrups. Isomerases are expensive and, therefore, any significant decrease in isomerase requirements would result in substantial cost reductions to the isomerized glucose syrup manufacturer. Also, an isomerase excess can readily lead to the formation of undesirable by-products which, unless removed therefrom, will reduce the quality and value of the isomerized syrup product. Removal of these by-product impurities necessitates additional processing steps, frequently lowers production capacity and results in increased capital equipment expenditures which adversely affects overall production costs.

Continuous fixed isomerase bed reactors are employed in producing a substantial percentage of the isomerized glucose syrups today. In continuous fixed bed reactor systems, the desired fructose level is obtained by permitting a high glucose containing syrup to flow through a bed of immobilized glucose isomerase or a series of reactor beds. Passage of the glucose containing syrup through the fixed isomerase beds is discontinued upon achieving the desired fructose conversion. The amount of fructose produced by a fixed bed reactor is directly proportional to its isomerase activity. Decreased yields inherently arise as a result of isomerase deactivation therein. The isomerase bed will ultimately deteriorate and become totally ineffective. Removal of the deactivated isomerase from the fixed bed or partial replenishment with fresh isomerase is necessary to insure continued fructose production. Periodic or frequent replacement of fresh isomerase substantially reduces overall isomerized glucose syrup capacity. To compensate for these problems, the isomerized glucose syrup producer may install relatively large fixed bed reactors or additional fixed bed reactors (an added capital expenditure), increase the number of passes of the glucose syrup through the bed, reduce glucose syrup flow rate through the fixed bed reactor and thereby increase the contact time therewith, utilize excessive amounts of isomerase in the beds (undesirable because it usually reduces bed flow rates and concomitant production of undesirable by-products) and such other corrective processing modifications.

Several alternatives have been proposed to overcome this isomerase deactivation problem. Many researchers deem the solution to isomerization deactivation problem as residing in the discovery of an organism which will produce a more stable form of isomerase. As a result, numerous existing organisms and new strains have been screened and isolated in the art's attempt to discover a more stable isomerase.

Immobilized isomerases have also been proposed as a means for inhibiting isomerase deactivation since free or water-soluble isomerases are relatively unstable. Heat or chemical treatment of viable cells containing intracellular isomerase, encapsulation, complexing of the isomerase with natural and synthetic polymers, immobilization of the enzyme within a binder matrix and numerous other forms of immobilizing the isomerases have been suggested.

It is also known that isomerases are less susceptible to deactivation when the isomerization reaction is conducted in the presence of one or more metal ion activators. The metal ion activators and the requirements will depend primarily upon the specific type of isomerase. When an isomerase is isolated from a new source or in a different form, it is conventional to establish its metal ion activator requirements.[1] Suppliers of commercial isomerases customarily provide technical information with respect to its metal ion activator requirements in a glucose isomerization process.

[1] - References cited herein are illustrative of the establishment of metal ion activator requirements in an isomerization process.

In the commercial production of enzymatically isomerized glucose syrups, the metal ion activator concentration is carefully controlled at a prescribed level. Excessive or insufficient metal ion activator concentrations are avoided. For the prolonged time intervals necessary to complete the isomerization reaction, an excessive amount of metal ion activator frequently represses isomerase efficacy (e.g., isomerase poisoning), can present health hazards (e.g., toxic), may impart undesirable flavor or color to isomerized glucose syrup as well as adversely affecting syrup stability, which necessitate additional refining or filtration processing steps to remove these impurities therefrom (e.g., ion exchange treatment). If the metal activator ion concentration is too low, stabilization against deactivation will not be achieved. Thus, it is customary for the isomerized glucose syrup producer to maintain the metal ion activator concentrations at the lowest possible level yet sufficiently high to preserve the isomerase's activity.

Certain isomerases require a sole metal ion activator whereas others evince greater stability when co-metal ion activators are present in the isomerization media. When co-metal ion activators have a stabilizing effect upon the isomerase, normally one metal ion activator will be essential while the other co-metal ion activator will not significantly increase the isomerase activity unless the required metal ion activator is also cooperatively present in the reaction media.

It has been reported that certain isomerases are activated by conducting the isomerization reaction in the presence of thiol activating reagents such as glutathione and cysteine (e.g., see J. Agri. Chem. Soc. Japan 36, No. 12, 1013–1016, 1962, by Y. Takasaki et al.; J. Biol. Chem. 218, 535, 1956 by M. J. Palleroni et al.; J. Am. Chem. Soc. 77, 1663, 1955 by M. W. Slein; and Agr. Biol. Chem. Vol. 28, No. 8, pp. 510–516, 1964 by M. Natake et al.). Many of the researchers have also reported that isomerase activity can be markedly decreased by conducting the isomerization reaction in the presence of sulfhydryl binding agents which react with the sulfhydryl group (e.g., cuprous ions such as cuprous sulphate or chloride, p-chloromercuribenzoate, monoidoacetate, mercurous ions, zinc sulphate, etc.). Conducting the isomerization reactions in the presence of oxidizing agents, including nascent oxygen, have also been reported as having an inhibitory effect upon isomerase activity.

OBJECTS

It is an object of this invention to activate a dry isomerase preparation and obtain an activated isomerase which possesses greater effectiveness in a monosaccharide isomerization process.

Another object of this invention is to increase the half-life of an isomerase preparation in a monosaccharide isomerization process.

A still further object is to provide a method for pretreating a dry glucose isomerase in an aqueous activating media to optimize its total isomerase activity and the isomerization of glucose syrups therewith.

An additional object of the invention is to reduce the isomerase volume and weight requirements in a glucose isomerization process.

Another object is to reduce the overall manufacturing costs in a glucose isomerization process.

DESCRIPTION OF THE INVENTION

According to the present invention, there is provided a method for increasing the isomerase activity of a dried isomerase preparation in an aqueous monosaccharide isomerization reaction, said method comprising initially pretreating a dry isomerase preparation with an aqueous activator comprised of water and at least one activating solute selected from the group consisting of metal ion activators for said isomerase, a water-soluble thiol activator for said isomerase and isomerizable monosaccharide for said isomerase, and continuing the pretreatment of said isomerase with said aqueous activator solution for a period of time sufficient to permit the isomerase to imbibe the aqueous activating solution and thereby saturate the isomerase with said activating solute and increase the isomerization activity of said isomerase.

Dry isomerase initially pretreated with aqueous activating solution possess unexpectedly improved isomerase activity when they are subsequently utilized in conventional monosaccharide isomerization processes. Comparative to the customary practice of admitting or admixing and hydrating the dry isomerases in an isomerization reaction media under conditions conducive to the isomerization of the monosaccharide to the monosaccharide isomer by the isomerase, isomerase activity can be effectively increased 20% or more by the pretreatment method of this invention.

The technical reasons why the pretreatment of a dry isomerase results in substantial improvements in the isomerase's activity is not fully understood. It is believed, however, the conventional practice of concentrating and drying of isomerases adversely affects the molecular configuration of isomerase and results in substantial isomerase deactivation. Apparently, intra- and/or intermolecular isomerase hydrogen bonding and possibly chemical reaction between the reactive groups within the isomerase molecule (e.g., chemical reaction of a thiol substituent with another substituent or another thiol site to form disulfide linkages) are established and formed during the concentration and drying thereof. Failure to restore the isomerase molecular configuration to its optimum and maximum state of isomerization activity is believed to be largely responsible for the art's inability to realize the total isomerization activity of isomerases which are derived from dry isomerase sources. The conventional practice of homogeneously dispersing either immobilized isomerase or water-soluble isomerase in water prior to introducing the isomerase into the isomerization reaction zone does not effectively develop or restore the isomerase to its maximum activity. Similarly, introducing the dry isomerase into the isomerization reaction media or prior hydration of the isomerase (in the presence or absence of metal ion activators and/or thiol activators and/or isomerizable monosaccharides) under conventional isomerization conditions does not effectively restore the latent isomerase sites to a highly active state.

The pretreating aqueous solutions employed in this invention contain at least one activating solute selected from the group of metal ion activators, water-soluble thiol activators and isomerizable monosacchrides in an amount sufficient to enhance the isomerase activity of the isomerase pretreated therewith. As mentioned hereinbefore (e.g., see references cited herein), certain metal ion activators are known to markedly improve upon the effectiveness of a glucose isomerase in a glucose isomerization process. Glucose isomerization processes are conventionally conducted in the presence of these metal ion activators. Occasionally two or more metal ion activators will cumulatively or synergistically increase the isomerase activity in a glucose isomerization reaction. The metal ion activator requirements for commercial isomerase in glucose isomerase processes will sometimes vary depending upon the particular strain and/or type of isomerase.

Any metal ion activator which enhances the isomerase's activity during the isomerization process may be utilized as a metal ion activator in the pretreatment step. If it is desired to pretreat an isomerase which possesses optimum isomerization functionality in the presence of two or more co-metal ion activators, the pretreatment step may be conducted in the presence of either one of the co-metal ion activators or any combination thereof. The metal ion activator may be used alone or in combination with an isomerizable monosaccharide and/or the thiol activator in the pretreatment step. Improved iosmerase activity results are achieved when the metal ion activators are used conjointly in the pretreatment step with at least one of the other activating solute groupings herein (i.e., isomerizable monosaccharide and/or thiol activators). The pretreatment of isomerase with the metal ion activators, isomerizable monosaccharides and thiol activators conjointly will provide the highest degree of isomerase activation.

As a general rule, the metal ion activators for isomerases (most commonly reported) have a valence of two and are most generally characterized as having an atomic number of 28 or less. The Period IIa metal ions (e.g., magnesium) and those metal ions of atomic Nos. 22–27 inclusive (particularly manganous, ferrous and cobalt) and mixtures thereof are most commonly used and reported as isomerase metal ion activators in an isomerization process. These metal ion activators form a metal complex with the isomerase and enable it to isomerize dextrose to fructose. Valence two metals having an atomic number 29 or greater (e.g., copper and zinc) generally deactivate the isomerases.

By predetermining the optimum metal ion activator molarity for any given isomerization reaction, the required amount of metal ion activator necessary to achieve maximum glucose isomerization with a particular iosmerase can be determined. In a glucose isomerization process, isomerase activity will proportionally increase when the metal ion activator molarity of isomerization media is incrementally increased until it reaches an optimum isomerization value at which point any additional increase in metal ion activator molarity will have a repressive effect upon the glucose isomerization reaction. More complete metal activator ion-isomerase complexing (with minimum isomerase degradation) is achieved when the pretreating aqueous solution contains a metal ion activator molarity substantially greater than the molarity required to achieve optimum fructose yields in the isomerization reaction. Accordingly, the metal ion activator molarity of the aqueous pretreating solution should be substantially above the optimum metal ion molarity of the isomerization reaction (i.e., at a metal ion molarity which will have a repressive effect upon glucose isomerization reaction). Typically, the molarity of the pretreating solution will be two times greater than the molarity normally employed in the isomerization reaction with further improvements in isomerase activity being achieved when the pretreatment solution contains at least a 10-fold molar excess thereover. Each isomerase molecule will complex with one metal activator ion in the reaction. Accordingly, the required amount of metal activator ion in the pretreating solution will proportionally increase with the amount of isomerase to be treated therewith. Although dry commercial isomerase preparation will normally contain a substantial amount of metal ion activator (e.g., in the complex form), more effective isomerase activity is accomplished by utilizing about a stoichiometric amount or higher amount of metal ion activator in the pretreatment solution (e.g., about one mole of isomerase for each mole of metal ion activator). Advantageously, 25% or more of the total metal ion activator requirements for isomerization process are used to pretreat the isomerase. Further improvements in isomerase activity will be achieved by utilizing an aqueous solution which contains more than 50% of the total isomerization media metal activator ion requirements at a molarity 25 times greater than that required for optimum isomerization reactivity. Preferably, the molarity of the pretreatment solution will exceed the isomerization reaction media by a factor of 50% with 75% or more of the total isomerization media metal ion activator requirements therefore being used in the pretreatment thereof.

Another class of pretreating solutes having a favorable effect in restoring a dry isomerase in a more active state is the isomerizable monosaccharides. The term "isomerizable monosaccharides" refers to those monosaccharides which the isomerase can isomerize. Accordingly, the isomerizable monosaccharides employed in the pretreating solution will depend upon the isomerization characteristics of the isomerases to be pretreated therewith. As a general rule, most glucose isomerases are capable of isomerizing certain pentoses (e.g., xylose and/or xylulose) as well as certain hexoses (e.g., dextrose and/or fructose). These isomerizable monosaccharides may be utilized in the pretreating solution. The isomerization of glucose with gluose isomerase is a reversible reaction (i.e., glucose $\underset{\text{isomerase}}{\rightleftharpoons}$ fructose). Accordingly, both glucose and fructose are isomerizable by glucose isomerase and may be employed as an isomerizable monosaccharide in the pretreatment solution. Glucose has been found particularly effective as a pretreating isomerizable monosaccharide. Under the pretreatment conditions of this invention, the isomerizable monosaccharide appears to form an isomerase-monosaccharide complex. When the isomerase-monosaccharide complex, which is formed by the pretreatment step herein, is utilized and exposed to isomerization reaction media at elevated temperatures, the isomerase complex tends to stabilize the isomerase against deactivation and enhance its overall effectiveness in the isomerization reaction.

The amount of isomerizable monosaccharide can vary considerably. Since each active isomerization site in an isomerase molecule can form a complex with a glucose molecule, one mole of glucose (or other isomerizable monosaccharide) for each mole of isomerase will normally be required when an isomerizable monosaccharide is employed as the sole pretreating solute. The pretreatment step is more effectively accomplished (with the least amount of deactivation) when the pretreating solution contains greater than 0.5 moles of isomerizable monosaccharide. At relatively high monosaccharide concentrations (e.g., 4 moles or higher) it is mechanicaly difficult to homogeneously disperse and pretreat the isomerase therein. Pretreating solution which contains from about 1 to about 4 moles of glucose (preferably about 2 to 3 molar monosaccharide aqueous solution) may be suitably used in the pretreatment step. Although the pretreating solution may contain the isomerizable monosaccharide by itself, maximum isomerase activation is achieved when it is used in combination with either the metal ion activator solutes and/or the thiol activators.

Another class of pretreatment reagents having a beneficial effect upon restoring previously dried isomerases to a higher degree of activity are thiol activators. The thiol activators, as a class, chemically react with isomerase disulfide linkages to provide thiol containing reaction products. Why these disulfide reducing agents increase isomerase activity is not fully understand. It is evident, however, that dry isomerases contain disulfide linkages in a form which adversely affects their enzymatic activity. The thiol activators which cleave isomerase disulfide linkages in equilibrium as illustrated by the following reaction:

$$RSSR + A^{2-} \rightleftharpoons RS^- + RSA^-$$

wherein RSSR represents an isomerase disulfide molecular linkage and A represents a reducing agent anion and are particularly effective thiol activators. Chemical reagents which are precursors for sulfite ions (e.g., an anion A for the above reaction) in aqueous solution can be used to effectively restore dry isomerase preparations to a highly active state. Such precursors include sulfur dioxide and the water-soluble salts of sulfurous acid in an amount sufficient to measurably increase the enzymatic activity above that level obtained by carrying out the pretreatment in the absence of sulfurous acid precursors. Illustrative water-soluble salts of sulfurous acid include the alkaline metal sulfites such as the potassium or sodium salts of sulfite, bisulfite, pyrosulfite, etc. as well as the corresponding water-soluble metal ion activator salts thereof (e.g., manganous, cobaltous and magnesium sulfite, bisulfite, etc.) with the latter functioning both as metal ion activators as well as thiol activators in the pretreating solution. Numerous other water-soluble $SO_3^=$ producing metal salts may also be used. However, isomerase deactivating metal salts of sulfurous acid (e.g., zinc, cupric, aluminum salts, etc.) should not be employed because these metal ions are known to form non-functional complexes therewith.

When thiol activators are employed, the amount of thiol activators should be sufficient to have a measurable effect upon the resultant iosmerase comparative to pretreatment thereof in the absence of these thiol activators. A small amount of thiol activator (e.g., about 0.05% anion weight or more on a total isomerase dry weight basis) will generally have a measurable effect upon activation. Sulfite anion concentrations substantially exceeding (e.g., 10% or higher anion dry weight percent) that amount necessary to establish the above equilibrium reaction (e.g., a stoichiometric amount) will not provide any further improvements upon isomerase activation but may be used for purposes of accelerating the rate at which the equilibrium reaction is achieved. Effective isomerase activation is generally achieved when the weight percent of sulfurous acid anion (on a dry isomerase weight basis) ranges from about 0.5 to about 5 and most effectively at about 2 to about 4 weight percent.

Prolonged pretreatment of the isomerase at elevated temperatures can, under certain conditions, frustrate the desired objective of increasing total isomerase activity. When pretreating temperatures of 45° C. or higher are employed, thermal deactivation of the isomerase can mitigate or exceed the benefits obtained by the isomerase pretreatment. At temperatures wherein the isomerase possess optimum isomerase activity (e.g., 50° C.+), thermal deactivation thereof can be effectively minimized or controlled by either reducing the pretreatment time interval or by conducting the pretreatment in the presence of a metal ion activator at a molarity substantially greater than that conventionally employed to achieve optimum glucose isomerization (e.g., see paragraph bridging pages 10 and 11 supra). Sulfite anion and glucose as conjoint pretreatment solutes will also further stabilize the isomerase against thermal deactivation.

Illustrative elevated pretreatment temperatures include about 5 minutes to less than one hour and preferably less than one half at 60°–65° C., about one and half hour and preferably less than one hour at 55°–60° C., and about one-half hour to about 5 hours and preferably about 1 to about 2 hours at 50°–55° C. Substantially improved isomerase activating results are obtained at pretreatment temperatures substantially below the optimum isomerization temperature of the isomerase. Accordingly, it is particularly advantageously to maintain the pretreatment solution at a temperature ranging from above the freezing point of pretreatment solution to less than 40° C. for about one half hour to about 2 days or more and preferably at a temperature of less than about 30° C. for about 2 hours to about 30 hours or more. At these reduced pretreatment temperatures, the isomerase activity is maintained at a low level without adversely effecting the ability of the isomerase to form the desired metal-glucose-isomerase complex even though the pretreatment may be conducted for longer periods of time. Optimum activation with the least amount of degradation to the isomerase is accomplished when the pretreatment is conducted for 3 or more hours at a temperature ranging from about 10° C. to about 25° C.

In column, fixed-bed isomerase reactors, isomerase pretreatment may be accomplished by in situ or by separately contacting the isomerase with the pretreating solution for a period of time sufficient to activate the isomerase (e.g., soaking in situ, passing pretreating solution therethrough or separately pretreating enzyme and placing pretreated isomerase in column). In batch and other continuous type of isomerization reaction systems, initial pretreatment of the isomerase prior to its placement in the isomerization reaction zone is usually desirable. The pretreatment step may be conducted by conventional means for saturating dry substances (e.g., soaking the isomerase with or without moderate mixing). The pretreatment step is most suitably conducted at dry isomerase solids levels substantially greater than the level normally used in the isomerization reaction medai (e.g., usually contain less than about 2.5% dry isomerase solids on total isomerization media weight basis). Broadly, the weight ratio of dry isomerase solids to pretreatment solution may range from about 1:100 to about 1:1 or higher. At the higher isomerase solids level, the pretreatment solution is difficult to handle while the lower solids level will normally necessitate excessive pretreatment periods to activate and additional processing thereof to convert it into a suitable form for the isomerization reaction. It is, therefore, advantageous to pretreat the isomerase at a weight ratio of dry isomerase to pretreating solution weight above 1:25 to less than about 2:3 and preferably between about 1:9 to about 1:2. The pretreating solution may contain the same weight proportion of dry isomerase to metal ion activator as conventionally used in the isomerization reaction excepting the concentration or molarity will be substantially higher.

Acidic or alkaline pretreating solute conditions leading to denaturization or degradation of the isomerase protein are not suitable. In general, the pH pretreatment may be conducted at a pH between about 5.5 to about 8.5 with a pretreatment at a pH of about 6.5 to about 7.5 being preferred.

The pretreatment method is generally applicable to dry isomerase obtained from a variety of microbial sources and in divergent forms such as water-soluble isomerases and/or insoluble isomerases and/or immobilized isomerase. Illustrative isomerase sources (including different dry isomerase forms thereof) include the glucose isomerases such as disclosed in British patent specification No. 1,274,158; West German patent specification No. 2,164,342 by K. Aunstrup et al.; U.S. Pat. No. 3,841,969 by A. N. Emery; U.S. Pat. No. 3,753,858 by Y. Takasaki; U.S. Pat. No. 3,821,082 by W. R. Lamm et al.; West German patent specification No. 2,345,185 by D. Louis; U.S. Pat. No. 3,779,869 by M. F. Zienty; U.S. Pat. Nos. 3,823,133 by Hurst et al., 3,788,945 by Thompson et al. and 3,694,314 and 3,817,832 by Lloyd et al. with the water-soluble or immobilized isomerases obtained from the Streptomyces and especially of the Bacillus genus are particularly adaptable to the pretreatment method of this invention. The aforementioned patents also illustrate the metal activator ion requirements for those divergent isomerases in a glucose isomerization process.

The pretreatment step (irrespective of whether an isomerizable monosaccharide or metal ion activator or thiol activator or any combination thereof is used as an aqueous pretreating solution) measurably increases isomerase activity in comparison to dry isomerases which have not been pretreated. Pretreatment with thiol activator will contribute to an isomerase activity increase of 5% or more with about a 10% to 20% increase being typically achieved thereby when it is combined with one other coactivator. Metal ion activator alone or with glucose can increase isomerase activity of a dry isomerase from about 5% to about 30% and usually between about 10% to about 25%. When a thiol activator and metal ion activators are conjointly used as pretreating solutes, an enzymatic activation increase of more than 15% can easily be achieved with increases ranging from about 15% to about 30% or higher being obtainable thereby. Isomerase pretreatment with glucose alone can effectively increase the isomerase activity by more than 10% and preferably above 15% (typically between about 10 to about 20% increase). The combination of glucose, thiol activator and metal activator increases iosmerase activity 10% or more with increases between about 15% to about 30% or more being most typically achieved thereby.

In the pretreatment of glucose isomerase, it is particularly desirable to utilize a pretreatment solution which contains the same metal ion activator as required by the isomerase in the isomerization reaction, preferably along with the full amount of sulfite therefore, with a minor portion of the glucose which is to be ultimately isomerized therewith. By employing a higher isomerase solids level, a higher molarity of metal ion activator and higher level sulfite ions concentration while retaining essentially the same glucose isomerase to metal ion activator weight ratio and thiol activator weight ratio, the pretreated isomerase as well as pretreating solution can be directly transferred to the reactor and employed as a total isomerase, metal ion activator and sulfite ion source for the isomerization reactor. For example, all the metal ion activator, all thiol activator requirements and all glucose isomerase requirements for a batch isomerization can be combined with 1% of the total glucose syrup to be isomerized therewith, pretreated in situ to achieve optimum isomerase activity and then directly transferred to a batch reactor which contains the remaining 99% of the glucose syrup. The glucose syrup can be directly isomerized to the desired isomerization product without requiring the addition of anything besides the glucose syrup. Alternatively, the pretreated isomerase may be partitioned from the pretreating solution and transferred in the hydrated form to the isomerization reactor. This alternative approach is occasionally beneficial when it is desired to reduce the total metal activator requirements in an isomerization reaction.

When dry glucose isomerases are pretreated and activated in accordance with this invention and employed in a conventional glucose isomerization process, the pretreated isomerase herein possesses enhanced isomerase activity and more effectively isomerizes glucose containing syrups to an isomerized glucose syrup product (i.e., a glucose-fructose syrup product). Excepting for the pretreatment and activation of the isomerase, the pH, temperature, time, metal ion requirements, isomerase units/gram glucose, ratio of isomerase to metal ion activator and glucose syrup dextrose content and other desired additives to optimize the isomerization reaction (e.g., thiol activator, etc.) and other isomerization reaction conditions as conventionally employed to obtain optimum fructose production and yields can be adapted to the production of an isomerized glucose syrup product with thiol and pretreated isomerases of this invention. Because the pretreated isomerase possesses a substantially improved isomerase activity, the isomerase will possess a higher degree of potency than an untreated isomerase and therefore the fructose produced by a given amount of dry isomerase will be substantially greater than that achieved by employing an equivalent weight percent of untreated dry isomerase.

The following examples are illustrative and should not be construed as limiting the scope of the invention.

EXAMPLE 1

A spray-dried, crude, isomerase broth obtained by cultivation and elaboration of isomerase by *Bacillus coagulans* was pretreated to enhance its isomerase activity. The spray dried isomerase broth (Novo SB 103 sold and distributed by Novo Industri, Copenhagen) contained both water-soluble and water-insoluble isomerase.

The pretreatment solution consisted of 100 milliliters of refined 95 D.E. glucose syrup (94% dextrose, d.s.b., and 50.5% total dry substance or 61.17 grams of dry solids), .02 M magnesium sulfate (as epsom salt), 0.001 M cobaltous nitrate, and 0.01 M sodium sulfite. To the pretreatment solution, 4.6 grams of the spray dried isomerase preparation was added, uniformly mixed therein for 30 minutes at a temperature of 23° C. and pH 6.3.

The pretreated isomerase and the pretreatment solution was then transferred to an isomerization reaction media consisting of 2,900 milliliters (60° C.) of refined 95 D.E. glucose syrup (50.5 dry solids or 1,773.83 grams dry solids) of a 94% dextrose content (d.s.b.) and adjusted to pH 6.4 with 10% aqueous sodium hydroxide. The total metal ion activator requirements (i.e., $Co^{++}$ and $Mg^{++}$) for the glucose isomerization reaction were provided by the pretreatment solution. Dilution of the pretreatment solution from 100 ml. to the 3,000 milliliters represents a 30-fold dilution of $Co^{++}$ and $Mg^{++}$ molarity. The optimum metal ion activator concentration for the isomerization reaction for this glucose isomerase was at this level. With gentle stirring while maintaining the glucose isomerization reaction at pH 6.4 and 60° C., the glucose containing syrup was isomerized to a glucose-fructose syrup product.

For comparative purposes, 4.6 grams of untreated dry isomerase was added to 3,000 milliliters (at 60° C.) glucose syrup and used to isomerize the glucose syrup of an identical composition under the same isomerization reaction conditions as above.

The amount of fructose (gms.), percent dextrose isomerized (based on 1,725 total grams of dextrose) to fructose after 24 hours and 48 hours for the pretreated isomerase and untreated isomerase is as follows:

|  | Pretreated Isomerase | | Untreated Isomerase | |
| --- | --- | --- | --- | --- |
| Time (hrs.) | Fructose (gms.) | % Fructose | Fructose (gms.) | % Fructose |
| 24 | 600.3 | 34.8 | 558.9 | 32.4 |
| 48 | 745.2 | 43.2 | 690 | 40.0 |

As illustrated above, the pretreated isomerase possessed a higher degree of isomerase activity and, therefore, was capable of isomerizing higher fructose yields than an equivalent amount of untreated dry iosmerase.

EXAMPLE 2

A dry isomerase preparation (0.826 grams) of the same type as employed in Example 1 was pretreated for 45 minutes, pH 7.0 at 23° C. in accordance with the methodology of Example 1 with 23 milliliters pretreating solution containing 20 milliliters of glucose syrup (52.8 d.s. at 94% dextrose on d.s.b.) and 0.001 M sodium sulfite plus 3 milliliters of aqueous 1 M $Mg^{++}$ and 0.15 milliliter of aqueous 1 M $Co^{++}$. The pretreated isomerase, including the pretreatment solution, was then employed to isomerize an additional 270 milliliters glucose syrup (58.2 d.s. at 94% glucose on a d.s.b.) by introducing the pretreated glucose isomerase and pretreating solution into an isomerization reaction maintained at 60° C. and pH 7.0. For comparative purposes, 0.826 grams of dry isomerase was directly added to an isomerization media of an identical composition and isomerized under the same conditions as with the pretreated isomerase immediately above. The results of this example are as follows:

| Time (hrs.) | Untreated Isomerase (Fructose gms.) | Pretreated Isomerase (Fructose gms.) | Pretreated Fructose % Increase |
| --- | --- | --- | --- |
| 6 | 4.9 | 6.8 | 139% |
| 35 | 9.6 | 14.0 | 146% |
| 70 | 11.1 | 15.2 | 136% |
| 94 | 13.0 | 16.4 | 126% |

As shown above, the pretreated isomerase produced more fructose in a shorter period and provided higher fructose yields in comparison to the untreated isomerase. The pretreated isomerase after 35 hours, produced more isomerized glucose (i.e., 14.0 grams fructose) than the untreated isomerase did after 94 hours isomerization.

EXAMPLE 3

An immobilized, dry isomerase preparation (1.062 grams) obtained from a Bacillus coagulans and immobilized in accordance with the teachings of West German patent specification No. 2,345,185 by Nova Terapeutisk Laboratorium and identified as Novo SB 113 A (sold and distributed by Novo Industri, Copenhagen) was pretreated by uniformly admixing the dry isomerase with a pretreating solution consisting of 20 ml. glucose syrup (58.2% dry solids, 14.6 grams D.S. of which 94% was glucose) at 0.001 M sodium sulfite and a 3 ml. aqueous solution of 1 M $Mg^{++}$ (magnesium sulfate) and 0.15 ml. of a 1 M $Co^{++}$ aqueous solution (as cobaltous nitrate) for 45 minutes at 23° C. An isomerization reactor was charged with 300 ml. glucose syrup having an identical composition as employed in the pretreatment step, heated to 60° C. at pH 6.8 and the pretreated isomerase and pretreatment solution were added thereto. The isomerization media was then maintained at pH 6.8 and 60° C. An identical dry weight of untreated dry isomerase was directly admixed into an isomerization media of an identical composition and permitted to isomerize the glucose syrup under the same isomerization conditions. The tabulated results of this example are as follows:

| Isomerization Time (hrs.) | Pretreated Isomerase (Fructose gms./ 100 gms. D.S.) | Untreated Isomerase (Fructose gms./ 100 gms. D.S. |
| --- | --- | --- |
| 6 | 7.8 | 6.5 |
| 35 | 28.0 | 24.8 |
| 70 | 37.0 | 34.0 |
| 94 | 39.6 | 37.1 |

EXAMPLE 4

A dry glucose isomerase (Streptomyces ATCC 21175) containing intracellular isomerase prepared in accordance with the example of U.S. Pat. No. 3,694,314 by N. E. Lloyd et al. was pretreated (1.5 grams dry isomerase) in 10 ml. of aqueous buffer (0.015 M acetate-pH 7.0) at 23° C. for 10 minutes in pretreating solutions containing varying amounts of metal ion activator and thiol activator. In the dry form, the isomerase contained 0.15% cobalt and 1.15% magnesium (d.s.b.). Pretreatment solutions A-D contained the following solutes (% given on dry enzyme basis): (A) $Co^{++}$ 0.33% and $Mg^{++}$ 1.33%, (B) 0.2% $Co^{++}$, 2% $Mg^{++}$ and 3.3% sodium sulfite, (C) 0.2% $Co^{++}$, 2% $Mg^{++}$ and 4% sodium sulfite and (D) 0.2% $Co^{++}$ and 2% $Mg^{++}$. The pretreatment solutions, including the pretreated isomerase, were used in the isomerization assay test below. For comparative purposes, 1.5 grams of untreated dry isomerase (identified as (E)) was added directly to the assays substrate.

For assays A, B, D and E, glucose isomerase activity was determined in an assay substrate consisting of 50 ml. deionized water containing 30 grams pure anhydrous glucose, 0.02 M magnesium sulfate, 0.001 M cobalt salt ion ($Co^{++}$), 0.2 M sodium maleate and 0.02 M sodium chloride adjusted to pH 6.5 with 10% sodium hydroxide of dilute aqueous hydrochloric acid. In assay C, the same assay substrate was used except that all the $Co^{++}$ and $Mg^{++}$ requirements were provided by the pretreatment solution. The glucose isomerization reaction, for assay purposes, was conducted for one hour at 65° C. in a shaker water bath employing 50 ml. assay substrate plus pretreatment solutions A-D as indicated, in 125 ml. Erlenmeyer flasks. The isomerization reaction was terminated by the addition of 5 ml. of glacial acetic acid. Fructose yields were determined by optical rotation in a 2d tube. Isomerase activity assay for the test samples A-E are as follows:

| Isomerization Assay Sample | Glucose Isomerase Units/Gm. Isomerase |
|---|---|
| A | 175 |
| B | 191 |
| C | 192 |
| D | 184 |
| E | 153 |

As illustrated by the assay A–E data, the pretreated glucose isomerase provided significantly higher activity values than the untreated dry glucose isomerase (i.e., (E)). Pretreatment in the presence of both the thiol activator and the metal activators ($Mg^{++}$ ion and $Co^{++}$ ion) provided the highest order of isomerase activity (i.e., 120.26%) in comparison to the untreated isomerase isomerization results. An increase in metal ion activator concentration (e.g., pretreatment solutions A and D) further enhanced total glucose isomerase activity by about 5%. The above results illustrate pretreatment and isomerase activation with thiol activators and metal ion activators without glucose.

EXAMPLE 5

Pursuant to the isomerase activity assay procedure of Example 4, 1.0 grams of dry isomerase (Nov. SB 113A) was pretreated, used to isomerize an isomerization assay substrate (one hour at 65° C. and pH 6.5 consisting of 0.02 M $Mg^{++}$, 0.001 M $Co^{++}$, 0.01 M $Na_2SO_3$, 0.2 M sodium maleate and 30 grams anhydrous glucose in 50 ml. deionized water. In each of the pretreating solutions of test samples F–N, 10 ml. of deionized water was used in combination with the pretreating solutes as tabulated below[2]. The balance of assay substrate additives were then added to the pretreatment media to provide an equivalent assay substrate for each of the test samples. The results of this example are as follows:

| Test Sample | Pretreatment Solution | Glucose Activity (GI-U/gm.) | Activity % Increase |
|---|---|---|---|
| F | Glucose 6 gms.[3] | 558 | 11.6 |
| G | Glucose 6 gms.[3] + 0.05 M $Mg^{++}$ | 568 | 13.6 |
| H | Glucose 6 gms.[3] + 0.5 M $SO_2$ | 566 | 13.2 |
| I | Glucose 6 gms.[3] +0.01 M $Co^{++}$ +0.1 M $SO_2$ + 0.2 M $Mg^{++}$ | 604 | 20.8 |
| J | Glucose 6 gms.[3] + 0.2 M $Mg^{++}$ +0.1 M $SO_2$ | 600 | 20.0 |
| K | pH 6.5 Buffer[4] + 0.2 M $Mg^{++}$ +0.1 M $SO_2$ + 0.1 M $Co^{++}$ | 532 | 6.4 |
| L | Glucose 6 gms.[3] + 0.01 M $Co^{++}$ | 582 | 16.4 |
| M | Glucose 6 gms.[3] + 0.01 M $Co^{++}$ +0.1 M $SO_2$ | 588 | 17.6 |
| N | Glucose 6 gms.[3] + 0.1 M $SO_2$ | 588 | 17.6 |
| O | none | 500 | 0 |

[2]The metal ion and $SO_2$ (as tabulated above) refer to the molarity thereof in the 10 ml. pretreating solution.
[3]Anhydrous glucose.
[4]Sodium maleate 0.2 M buffer at pH 6.5.

As shown above, the pretreatment of dry isomerase significantly improves upon the total glucose isomerase.

What is claimed is:

1. A method for converting a dry isomerase to a hydrated isomerase to increase isomerase activity and enhance the effectiveness of the hydrated isomerase in an aqueous monosaccharide isomerization reaction, said method comprising initially pretreating a dry isomerase by contacting the dry isomerase with an aqueous activating solution comprised of water and at least one metal ion activator for said isomerase at a molarity substantially greater than the metal ion activator molarity required to provide optimum fructose yields in a glucose isomerization reaction with said isomerase, in combination with at least one solute selected from the group consisting of water-soluble thiol group activator for said isomerase and isomerizable monosaccharide for said isomerase in an amount greater than 0.5M, and continuing the pretreatment of said isomerase with said aqueous activating solution for a period of time sufficient to permit the isomerase to imbibe the aqueous activating solution and to saturate the isomerase with said activating solution and thereby increase the isomerization activity of said isomerase.

2. The method according to claim 1 wherein the isomerase is glucose isomerase.

3. The method according to claim 2 wherein the molarity of said metal ion activator in the aqueous activating solution is at least two times greater than the metal ion activator molarity required to provide optimum fructose yields in a glucose isomerization reaction with said isomerase.

4. The method according to claim 3 wherein the pretreating aqueous solution contains at least one metal ion activator having a plus 2 valence selected from the group consisting of magnesium and metal ions of an atomic No. 24–27 inclusive.

5. The method according to claim 2 wherein the thiol group activator comprises sulfite ions and the isomerizable monosaccharide comprises glucose in an amount ranging from about 1M to about 4M.

6. The method according to claim 5 wherein the pretreatment solution contains a weight ratio of dry isomerase solids to pretreating solution ranging from 1:25 to less than about 2:3 and the pretreatment pH ranges from about 5.5 to about 8.5.

7. The method according to claim 6 wherein molarity of the metal ion activator in the pretreatment solution is at least 10 times greater than the molarity at which the isomerase exhibits optimum isomerase activity in a glucose isomerization reaction.

8. The method according to claim 2 wherein the aqueous pretreatment solution is comprised of glucose at about 1 to about 3 molar concentration, a sulfite ion and at least one metal activator selected from the group consisting of $Co^{++}$, $Mg^{++}$ with the pretreatment of said dry isomerase being conducted for a period of time and at temperatures sufficient to increase the isomerase unit activity (on a one hour assay basis) by at least 20% in comparison to an equivalent weight of untreated isomerase which is directly added in the dry form to an isomerization assay media at a temperature of 65° C.

9. The method according to claim 2 wherein the dry isomerase solids to pretreatment solution weight ratio ranges from about 1:9 to about 1:2 and the pretreatment solution contains as solutes from about 2M to about 3 M glucose, sulfite anions in an amount more than about 1 weight percent of the dry isomerase solids weight and at least one metal ion activator at a molar concentration at least two times greater than the optimum metal ion molarity required to provide optimum fructose yields in a glucose isomerization reaction with said isomerase.

10. The method according to claim 9 wherein the pretreatment is conducted at a temperature of less than 40° C.

11. In a process for isomerizing an aqueous monosaccharide solution to an isomerized syrup product wherein an isomerase which has been previously dried and thereafter converted to hydrated isomerase is used as an isomerase in the isomerization reaction, and the isomerase is characterized as having enhanced isomerase activity when the isomerization reaction is conducted in the presence of at least one metal ion activator at an isomerization temperature in excess of 50° C., the improvement which comprises the steps of:
   A. pretreating the isomerase by saturating the isomerase with an aqueous solution comprised of at least one metal ion activator at a molarity substantially greater than the metal ion activator molarity required to provide optimum fructose yields in a glucose isomerization reaction with said isomerase, in combination with at least one solute selected from the group consisting of water-soluble thiol group activator for said isomerase and isomerizable monosaccharide for said isomerase in an amount greater than 0.5M, and continuing the pretreatment of said isomerase in said aqueous solution for a period of time sufficient to saturate the isomerase with the aqueous pretreating solution and substantially increase the isomerase activity of said isomerase, and
   B. isomerizing an aqueous monosaccharide solution with the pretreated isomerase to provide an isomerized syrup product,
with the molarity of said metal ion activator in pretreatment step (A) being substantially greater than the molarity of the metal ion activator employed in the isomerization of the monosaccharide in step (B).

12. The process according to claim 11 wherein the isomerase is glucose isomerase and a glucose syrup is isomerized to a fructose-containing syrup product.

13. The process according to claim 12 wherein the molarity of said metal ion activator in pretreatment step (A) is at least two times greater than the molarity of the metal ion activator employed in the isomerization of glucose in step (B).

14. The method according to claim 12 wherein the pretreating aqueous solution contains at least one metal ion activator solute having a plus 2 valence and selected from the group consisting of magnesium and a metal ion of an atomic No. 24–27 inclusive, the metal ion activator molarity in the pretreatment solution in step (A) is at least 10 times greater than the molarity of the aqueous solution of step (B) and the glucose syrup is isomerized to an isomerized glucose syrup product containing about 1 to about 2 parts by weight glucose for each part by weight fructose.

15. The process according to claim 12 wherein the pretreating solution contains a weight ratio of dry isomerase solids to pretreating solution ranging from 1:25 to less than about 2:3 and the pretreatment is conducted at a pH ranging from about 5.5 to about 8.5 and the thiol group activator comprises sulfite ions and the isomerizable monosacchride comprises glucose in an amount ranging from about 1M to about 4M.

16. The process according to claim 12 wherein the aqueous pretreatment solution is comprised of glucose at about 0.5 to about 3 molar concentration, sulfite anion in an amount ranging from about 0.5 to about 5.0 weight percent of the dry isomerase solids weight and at least one metal activator selected from the group consisting of $Co^{++}$, $Mg^{++}$ and $Mn^{++}$ with the pretreatment of said dry isomerase being conducted for a period of time and at temperatures sufficient to increase the isomerase unit activity (on a one hour assay basis) by at least 20% in comparison to an equivalent weight of untreated isomerase which is directly added in the dry form to the isomerization assay media at a temperature of 65° C.

17. The method according to claim 16 wherein the dry isomerase solids to pretreatment solution weight ratio ranges from about 1:9 to about 1:2 and the pretreatment solution contains at least one metal ion activator at a molar concentration at least two times greater than the optimum metal ion molarity required to provide optimum fructose yields in glucose isomerization step (B).

18. The method according to claim 17 wherein the pretreatment is conducted at a temperature of less than 40° C.

* * * * *

UNITED STATES PATENT AND TRADEMARK OFFICE
CERTIFICATE OF CORRECTION

PATENT NO. : 4,026,764

DATED : May 31, 1977

INVENTOR(S) : Thomas L. Hurst

It is certified that error appears in the above-identified patent and that said Letters Patent are hereby corrected as shown below:

Column 1, line 15; for "deactivation" read ---deactivate---
Column 6, line 63; for "understand" read ---understood---
Column 8, line 38; for "medai" read ---media---
Column 11, line 63; for "Nova" read ---Novo---
Column 13, line 26; for "(Nov." read ---Novo---
Column 13, bridging lines 41 and 42; for "(GI-U/gm.)" read ---(GIU/gm.)---
Column 13, line 49; for "0.1 M $Co^{++}$" read ---0.01 M $Co^{++}$---
Column 14, line 47; for "$Mg^{++}$ with" read ---$Mg^{++}$ and $Mn^{++}$ with---
Column 16, line 16; for "monosacchride" read ---monosaccharide---

Signed and Sealed this

*Twentieth* Day of *December 1977*

[SEAL]

Attest:

RUTH C. MASON
*Attesting Officer*

LUTRELLE F. PARKER
*Acting Commissioner of Patents and Trademarks*